US006423546B1

(12) United States Patent
Lusk et al.

(10) Patent No.: US 6,423,546 B1
(45) Date of Patent: Jul. 23, 2002

(54) MONOCLONAL ANTIBODIES FOR ASSAYING LIPID TRANSFER PROTEINS

(75) Inventors: Lance T. Lusk; Alfonso L. Navarro, both of Milwaukee; Henry Goldstein, Brookfield; Randall J. Wagner, New Berlin; David S. Ryder, Mequon, all of WI (US)

(73) Assignee: Miller Brewing Company, Milwaukee, WI (US)

( * ) Notice: Subject to any disclaimer, the term of this patent is extended or adjusted under 35 U.S.C. 154(b) by 0 days.

(21) Appl. No.: 09/705,221

(22) Filed: Nov. 2, 2000

(51) Int. Cl.$^7$ ............................................. G01N 33/543

(52) U.S. Cl. ........................ 435/792; 435/7.1; 435/975; 436/547; 436/548; 436/808; 530/388.1; 530/866; 530/864

(58) Field of Search ........................ 435/7.1, 975, 7.92; 436/547, 548, 808; 530/388.1, 866, 864

(56) References Cited

FOREIGN PATENT DOCUMENTS

| EP | 0 728 188 B1 | 8/1996 |
|---|---|---|
| EP | 0 863 153 A2 G | 9/1998 |
| WO | WO95/13359 | 5/1995 |

OTHER PUBLICATIONS

Bamforth, C.W. "Foam: Method, Myth or Magic," *The Brewer* 396–399 (Oct., 1995).
Bech et al., "Throughout the brewing process barely lipid transfer protein 1 (LTP1) is transformed into a more foam–promoting form," *Proc. Eur. Brew. Conv.* 561–568 (EBT Congress 1995).
Bock et al., (with English transcript of designated excerpts from pp. 52–54), "New Analytical Techniques with Relevance for the Brewing Industry," *Brygmesteren* 54(5):47–55 (1997).
Curioni et al., "Major Proteins of Beer and Their Precursors in Barley: Electrophoretic and Immunological Studies," *J. Agric. Food Chem.* 43:2620–2626 (1995).
Dahl et al., "Heterologous expression of Three Plant Serpins with Distinct Inhibitory Specificities," *J. of Biol. Chem.* 271(41):25083–25088 (1996).
Dickie, Kamini, "Immunological Determination of Foam–positive Hydrophobic Polypeptides in Barley and the Effects of Malting," *Brewing Research International Quarterly*, 15–18 (Oct.1997).
Donhauser, S., "Die Anwendung immunologischer Methoden in der Brauerei–Analytik," *Brauwelt* 116 (47):1560–1568 (1976) (with English abstract).
Evans, D.E., and Hejgaard, J., "The Impact of Malt Derived Proteins on Beer Foam Quality. Part I. The Effect of Germination and Kilning on the Level of Protein Z4, Protein Z7 and LTP1," *J. Inst. Brew.*, 105:156–169 (1999).

Evans, D.E., and Hejgaard, J., "The Impact of Malt Derived Proteins on Beer Foam Quality. Part II. The Influence of Malt Foam–positive Proteins and Non–Starch Polysaccharides on Beer Foam Quality," *J. Inst. Brew.* 105:171–177 (1999).
Evans et al., "The Importance of Protein Z to the Quality of Barley and Malt for Brewing," *Malting and Brewing Process*, 225–233 (EBC Congress 1995).
Evans et al., "Quantitation of Barley Derived Beer Foam–Positive Proteins in Barley and Malt by ELISA," (Australia Barley Tech. Symp. 1997).
Evans et al., "Quantitation of Barley Derived Beer Foam–Positive Proteins in Barley and Beer by Colorimetric Assays, Amino Acid Analysis and ELISA" (Poster).
Gibson et al., "Protein Z4 and Beer Foam," *Ferment* 9(2):81–84 (1996).
Gibson et al., "The Importance of Protein Z in Beer Foam," *Inst. of Brew.* (Asia Pacific Section 1996) (Poster Abstracts).
Hebert, J.P. and Strobbel B., "Evolution du probléme de la mousse de la biére," *Bios* 3(12):592–600 (1972) (with English summary).
Hejgaard, J., "Gene Products of Barley Chromosomes 4 and 7 Are Precursors of the Major Antigenic Beer Protein," *J. Inst. Brew.* 90:85–87 (1984).
Hejgaard, J. and Kaersgaard, K., "Purification and Properties of the Major Antigen Beer Protein of Barley Origin," *J. Inst. Brew.*, 89:402–410 (1983).
Hofstra, H., "Recombinant DNA en monoclonale antilichamen in gerst–, mout– en bieranalyse," *Voedingsmiddelentechnologie* 20(13):11–13 (1987) (with English abstract).
Horiuchi et al., "Determination of Beer Foam Protein by ELISA L Enzyme–Linked Immunosorbent Assay," *Inst. of Brew.*, (Asia Pacific Section, Proceedings of the Twenty–Third Convention, 1994) (Poster).
Ishibashi et al., "Application of ELISA to Quantitative Evaluation of Foam–Active Protein in the Malting and Brewing Processes," *J. Am Soc. Brew. Chem.* 55(1):20–23 (1997).
Ishibashi et al., "Development of a New Method for Determining Beer Foam and Haze Proteins by Using the immunochemical Method ELISA," *J. Am Soc. Brew. Chem.* 54(3):177–182 (1996).
Kaersgaard, K. and Hejgaard, J., "Antigenic Beer Macromolecule An Experimental Survey of Purification Methods," *J. Inst. Brew.*, 85:103–111 (1979).
Kauffman et al., "Immunological Characterisation of Barley Polypeptides in Lager Foam," *J. Sci. Food Argic.* 66:345–355 (1994).

(List continued on next page.)

Primary Examiner—Bao-Thuy L. Nguyen
(74) Attorney, Agent, or Firm—Quarles & Brady LLP

(57) ABSTRACT

The present invention relates to novel monoclonal antibodies reactive with lipid transfer proteins typically found in foaming beverages. More specifically, the present invention relates to novel monoclonal antibodies raised against the native and denatured forms of barley lipid transfer protein 1, and an assay for determining the content of said proteins in foaming beverages at various stages of their production.

7 Claims, 10 Drawing Sheets

OTHER PUBLICATIONS

Kakui et al., "Development of Monoclonal Antibody Sandwich–ELISA for Determination of Beer Foam–Active Proteins," *J. Am. Soc. Brew. Chem., Inc.* 56(2):43–46 (1998).

Lusk, et al., "Independent Role of Beer Proteins, Melanoidins and Polysaccharides in Foam Formation," *J. Am. Soc. Brew. Chem.* 53(3):93–103 (1995).

Lusk et al., "Foam Tower Fractionation of Beer Proteins and Bittering Acids," European Brewery Convention Beer Foam Quality Symposium, Amsterdam, The Netherlands (1998).

Mills et al., "Immunological Study of Hydrophobic Polypeptides in Beer," *J. Agric. Food Chem.* 46:4475–4483 (1998).

Offizorz et al., "Immunochemical Detection of Adjuncts in Beer. Part 1: Development and characterization of specific antisera," Monatsschrift für Brauwissenschaft 41(7):276–280 (1988) (English abstract).

Offizorz et al., "Immunochemical Detection of Adjunts in Beer. Part 2: Use of specific antisera to detect maize and rice adjuncts," Monatsschrift für Brauwissenschaft 41(8):319–323 (1988) (English abstract).

Offizorz et al., "Immunochemischer Nachweis von Rohfrucht in Bier," Monatsschrift für Brauwissenschaft 41(9): 360–365 (1988) (English abstract).

Onishi, A. and Proudlove, Michael O., "Isolation of Beer Foam Polypeptides by Hydrophobic Interaction Chromatography and their Partial Characterisation," *J. Sci. Food Agric.* 65:233–240 (1994).

Onishi et al., "Barley lipid–binding proteins: their role in beer foam stabilization," *Proc. Eur. Brew. Conv.* 553–560 (EBC Congress 1995).

Onishi et al. "Monoclonal Antibody Probe for Assessing Beer Foam Stabilizing Proteins," *J. Argic. Food Chem.* 47: 3044–3049 (1999).

Sheehan, M.C. and Skerritt, J.H., "Identification and Characterisation of Beer Polypeptides Derived From Barley Hordeins," *J. Inst. Brew.* 103:297–306 (1997).

Sorensen et al., "Barley Lipid Transfer Protein 1 is Involved in Beer Foam Formation," *MBAA Technical Quarterly* 30:136–145 (1993).

Sorensen, Steen Bech and Ottesen, Martin, "Fractionation and Characterization of Beer Proteins," *Carlsberg Res. Commun.* 43:133–144 (1978).

Vaag, P. and Munck, L., "Immunochemical Methods in Cereal Research and Technology," *Cereal Chem.* 64(2):59–72 (1987).

Winnewisser, W., and Donhauser, S., "Anwendung und Bedeutung immunchemischer Methoden in der Brauerei–Analytik," *Weihenstephaner* 60(3):177–181 (1992) (English abstract).

Yokoi et al., "Hydrophobic Beer Proteins and Their Function in Beer Foam," *J. Am. Soc. Brew. Chem.* 52(3):125–126 (1994).

Yokoi et al., "Characterization of beer proteins responsible for the foam of beer," Proc. Eur. Brew. Conv. 593–600 (EBC Congress 1989).

SEQUENCE LISTING

<160> NUMBER OF SEQ ID NOS: 17

<210> SEQ ID NO 1
<211> LENGTH: 91
<212> TYPE: PRT
<213> ORGANISM: Hordeum vulgare

<400> SEQUENCE: 1

Leu Asn Cys Gly Gln Val Asp Ser Lys Met Lys Pro Cys Leu Thr Tyr
1               5                   10                  15

Val Gln Gly Gly Pro Gly Pro Ser Gly Glu Cys Cys Asn Gly Val Arg
            20                  25                  30

Asp Leu His Asn Gln Ala Gln Ser Ser Gly Asp Arg Gln Thr Val Cys
        35                  40                  45

Asn Cys Leu Lys Gly Ile Ala Arg Gly Ile His Asn Leu Asn Leu Asn
    50                  55                  60

Asn Ala Ala Ser Ile Pro Ser Lys Cys Asn Val Asn Val Pro Tyr Thr
65                  70                  75                  80

Ile Ser Pro Asp Ile Asp Cys Ser Arg Ile Tyr
                85                  90

<210> SEQ ID NO 2
<211> LENGTH: 17
<212> TYPE: PRT
<213> ORGANISM: Hordeum vulgare

<400> SEQUENCE: 2

Leu Asn Cys Gly Gln Val Asp Ser Lys Met Lys Pro Cys Leu Thr Tyr
1               5                   10                  15

Val

<210> SEQ ID NO 3
<211> LENGTH: 17
<212> TYPE: PRT
<213> ORGANISM: Hordeum vulgare

<400> SEQUENCE: 3

Val Asp Ser Lys Met Lys Pro Cys Leu Thr Tyr Val Gln Gly Gly Pro
1               5                   10                  15

Gly

<210> SEQ ID NO 4
<211> LENGTH: 17
<212> TYPE: PRT
<213> ORGANISM: Hordeum vulgare

<400> SEQUENCE: 4

Lys Pro Cys Leu Thr Tyr Val Gln Gly Gly Pro Gly Pro Ser Gly Glu
1               5                   10                  15

Cys

<210> SEQ ID NO 5
<211> LENGTH: 17
<212> TYPE: PRT
<213> ORGANISM: Hordeum vulgare

<400> SEQUENCE: 5

Tyr Val Gln Gly Gly Pro Gly Pro Ser Gly Glu Cys Cys Asn Gly Val
1               5                   10                  15

Arg

<210> SEQ ID NO 6
<211> LENGTH: 17
<212> TYPE: PRT
<213> ORGANISM: Hordeum vulgare

<400> SEQUENCE: 6

```
Pro Gly Pro Ser Gly Glu Cys Cys Asn Gly Val Arg Asp Leu His Asn
 1               5                  10                  15
Gln
```

<210> SEQ ID NO 7
<211> LENGTH: 17
<212> TYPE: PRT
<213> ORGANISM: Hordeum vulgare

<400> SEQUENCE: 7

```
Glu Cys Cys Asn Gly Val Arg Asp Leu His Asn Gln Ala Gln Ser Ser
 1               5                  10                  15
Gly
```

<210> SEQ ID NO 8
<211> LENGTH: 17
<212> TYPE: PRT
<213> ORGANISM: Hordeum vulgare

<400> SEQUENCE: 8

```
Val Arg Asp Leu His Asn Gln Ala Gln Ser Ser Gly Asp Arg Gln Thr
 1               5                  10                  15
Val
```

<210> SEQ ID NO 9
<211> LENGTH: 17
<212> TYPE: PRT
<213> ORGANISM: Hordeum vulgare

<400> SEQUENCE: 9

```
Asn Gln Ala Gln Ser Ser Gly Asp Arg Gln Thr Val Cys Asn Cys Leu
 1               5                  10                  15
Lys
```

<210> SEQ ID NO 10
<211> LENGTH: 17
<212> TYPE: PRT
<213> ORGANISM: Hordeum vulgare

<400> SEQUENCE: 10

```
Ser Gly Asp Arg Gln Thr Val Cys Asn Cys Leu Lys Gly Ile Ala Arg
 1               5                  10                  15
Gly
```

<210> SEQ ID NO 11
<211> LENGTH: 17
<212> TYPE: PRT
<213> ORGANISM: Hordeum vulgare

<400> SEQUENCE: 11

```
Thr Val Cys Asn Cys Leu Lys Gly Ile Ala Arg Gly Ile His Asn Leu
 1               5                  10                  15
```

Asn

<210> SEQ ID NO 12
<211> LENGTH: 17
<212> TYPE: PRT
<213> ORGANISM: Hordeum vulgare

<400> SEQUENCE: 12

Leu Lys Gly Ile Ala Arg Gly Ile His Asn Leu Asn Leu Asn Asn Ala
 1               5                  10                  15

Ala

<210> SEQ ID NO 13
<211> LENGTH: 17
<212> TYPE: PRT
<213> ORGANISM: Hordeum vulgare

<400> SEQUENCE: 13

Arg Gly Ile His Asn Leu Asn Leu Asn Asn Ala Ala Ser Ile Pro Ser
 1               5                  10                  15

Lys

<210> SEQ ID NO 14
<211> LENGTH: 17
<212> TYPE: PRT
<213> ORGANISM: Hordeum vulgare

<400> SEQUENCE: 14

Leu Asn Leu Asn Asn Ala Ala Ser Ile Pro Ser Lys Cys Asn Val Asn
 1               5                  10                  15

Val

<210> SEQ ID NO 15
<211> LENGTH: 17
<212> TYPE: PRT
<213> ORGANISM: Hordeum vulgare

<400> SEQUENCE: 15

Ala Ala Ser Ile Pro Ser Lys Cys Asn Val Asn Val Pro Tyr Thr Ile
 1               5                  10                  15

Ser

<210> SEQ ID NO 16
<211> LENGTH: 17
<212> TYPE: PRT
<213> ORGANISM: Hordeum vulgare

<400> SEQUENCE: 16

Ser Lys Cys Asn Val Asn Val Pro Tyr Thr Ile Ser Pro Asp Ile Asp
 1               5                  10                  15

Cys

<210> SEQ ID NO 17
<211> LENGTH: 17
<212> TYPE: PRT
<213> ORGANISM: Hordeum vulgare

```
-continued

<400> SEQUENCE: 17

Val Asn Val Pro Tyr Thr Ile Ser Pro Asp Ile Asp Cys Ser Arg Ile
 1               5                  10                  15
Tyr
```

MONOCLONAL ANTIBODIES FOR ASSAYING LIPID TRANSFER PROTEINS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to novel monoclonal antibodies reactive with lipid transfer proteins typically found in foaming beverages. More specifically, the present invention relates to novel monoclonal antibodies raised against the native and denatured forms of barley lipid transfer protein 1, and an assay for determining the content of said proteins in foaming beverages at various stages of their production.

Foaming beverages, e.g. beer and some soft drinks, are popular items in today's marketplace. In addition to taste, the appearance of the beverage and its ability to form a stable head of foam when poured are important characteristics. In beer, the foam head is one of the first characteristics that a consumer generally uses to judge beer quality.

Foam formation and retention are two factors considered when defining foam quality. The rate at which the foam head forms and collapses depends upon, among other things, the composition of the beer.

Several different beer and foam proteins have been suggested to be important in foam formation and head retention. One such protein is the lipid transfer protein found in cereal grains. In particular, several different studies have analyzed the lipid transfer protein from barley and have shown that its presence in beer exhibits a positive effect on foam formation and stability. Evans and Hejgaard, "The Impact of Malt Derived Proteins on Beer Foam Quality. Part I: The Effect of Germination and Kilning on the Level of Protein Z4, Protein Z7, and LTP1", *J. Inst. Brewing*, 105:3:159–169 (1999); Evans et al., "The Impact of Malt Derived Proteins on Beer Foam Quality. Part I: The Influence of Malt-positive Proteins and Non-starch Polysaccharides on Beer Foam Quality", *J. Inst. Brewing*, 105:2:171–177 (1999); Lusk et al., "Foam tower fractionation of beer proteins and bittering acids," European Brewery Convention Beer Foam Quality Symposium (Amsterdam, Oct. 25–27, 1998); Bock et al., "New Analytical Techniques with Relevance for the Brewing Industry", *Brygmesteren*, 54(5):47–55 (1997); Lusk et al., "Independent role of beer proteins, melanoidins and polysaccharides in foam formation," *J. Am. Soc. Brew. Chem.*, 53(3):93–103 (1995); Sorenson et al., "Barley Lipid Tranfer Protein 1 is Involved in Beer Foam Formation", *MBAA Tech. Quarterly*, 30:136–145 (1993).

Two members of the lipid transfer protein gene family are expressed in barley grain, LTP1 and LTP2. Of the two proteins, only LTP1 is found in beer (see, Evans and Hejgaard, supra). LTP1 is an albumin protein primarily expressed in the aleurone layer of the barley seed. It has a molecular weight of 9,694 Daltons and contains 91 amino acid residues, including 8 cysteines. The amino acid sequence of LTP1 is set forth in SEQ ID NO:1. Studies by Bock et al., supra, have shown that LTP1 is modified during the malting and brewing process to a denatured form (fLTP). It is this denatured form that is believed to effect foam formation and stability.

Other studies have suggested that other proteins and polypeptides are important in foam formation and stability. In particular, it has been suggested that beer and foam proteins of a molecular weight greater than 5,000 Dalton tend to be foam-positive, while polypeptides of molecular weights below 5,000 Dalton tend to be foam-negative. For example, studies by Sharpe et al. have suggested that head retention was related to the ratio of high and low molecular weight polypeptides. (Sharpe et al., "Rapid methods of measuring the foam-active nitrogenous components of worts and beers", *Proc. Eur. Brewing Conv.*: 18th Cong., 607–614 (1981)). Meanwhile, Yokoi, et al, has suggested that protein Z, a 40,000 Dalton barley albumin, plays the most significant role in foaming and head retention (Yokoi et al., "Characterization of beer proteins responsible for the foam of beer", *Proc. Eur. Brewing Conv.*: 22nd Cong., 503–512 (1989)). On the other hand, Kauffman et al. has suggested that the prolamin storage proteins of barley, called hordeins, are also important in foam formation and stability (Kauffman et al., "Immunological Characterisation of Barley Polypeptides in Lager Foam", *J. Sci. Food Agric.*, 66:345–355 (1994)).

Most of the above conclusions have resulted from investigations generally involving the fractionation of beer proteins and a determination of their foaming effect. More recently, there has been considerable interest in tracing the origin of foam proteins using immunological methods. Polyclonal antibodies against barley, malt, beer and yeast proteins have been developed and used in these studies. For example, Hollemans and Tonies used polyclonal antibodies to remove polypeptides from beer to establish their effect on foaming (Hollemans and Tonies, "The role of specific proteins in beer foam", *Proc. Eur. Brew. Conv.*: 22nd Cong., 561–568 (1989)); Ishibashi et al., used polyclonal antibodies to analyze both foam and haze proteins in beer (Ishibashi et al., "Development of a new method for determining beer foam and haze proteins by using the immunochemical method ELISA", *J. Am. Soc. Brew. Chem.*, 54(3):177–18)); and Bech et al. used polyclonal antibodies to determine the concentration of LTP1 in wort, beer, and barley and malt extracts from several different barley varieties (EP 0728188). The information obtained using polyclonal antibodies, however, is partly limited due to problems of polyspecificity resulting from the presence of immunodominant repetitive hordein sequences (Mills et al., "Immunological Study of Hydrophobic Polypeptides in Beer", *J. Agric. Food Chem.*, 46:4475–4483 (1998)). Accordingly, more exact methods for performing immunological studies on beer and foam proteins are needed.

Monoclonal antibodies have been employed in some cases to avoid the problems associated with the use of polyclonal antibodies. For example, Kaufman et al., supra, has reported the use of monoclonal antibodies against wheat prolamins to study hordein-type material found in beer and foam fractions. Sheehan and Skerritt have also used monoclonal antibodies to examine modifications of hordeins during beer production (Sheehan and Skerritt, "Identification and Characterisation of Beer Polypeptides Derived from Barley Hordeins", *J. Inst. Brew.*, 103:297–306 (1997)). Mills et al. have reported the creation of a monoclonal library to beer proteins and polypeptides believed to be derived from the hordeins in malts (Mills et al., "Immunological Study of Hydrophobic Polypeptides in Beer", *J. Agric. Food Chem.*, 46:4475–4483 (1998)). Meanwhile, European Patent 0863153 by Ishibashi et al., and Kukai et al., "Development of Monoclonal Antibody Sandwich-ELISA for Determination of Beer Foam-Active Proteins",

*J. Am. Soc. Brew. Chem.*, 56(2):43–46 (1998), both report the production and use of monoclonal antibodies in ELISA experiments directed against foam-active proteins having molecular weights between 40 and 50 kDa.

With respect to the lipid transfer proteins, only a single monoclonal antibody disclosed by Dickie has been reported (Dickie, "Immunological Determination of Foam-Positive Hydrophobic Polypeptides in Barley and the Effects of Malting", *BRI Quarterly*, 15–18 (October, 1997)). This antibody, identified as IFRN 1625, recognizes a ca. 8 kDa polypeptide found in Group 5 foam fractions, and is believed to be one of the proteins involved in lipid transfer. Dickie postulates that this 8 kDA polypeptide originates from LTP1 but presents no evidence to support this hypothesis.

What is needed is a set of monoclonal antibodies exhibiting specificity against lipid transfer proteins in either their native or modified forms. What is also needed is an assay capable of measuring and characterizing the content of native and denatured lipid transfer proteins in foaming beverages during various stages of their production process.

BRIEF SUMMARY OF THE INVENTION

The present invention is summarized in that novel monoclonal antibodies against the native and denatured forms of barley lipid transfer protein 1 have been isolated.

The present invention includes monoclonal antibodies against the native form of barley lipid transfer protein 1 (LTP1). The first LTP1 antibody, identified as 3F7.1, has very strong reactivity to LTP1, no reactivity to fLTP and no reactivity to Protein. Z. Epitope mapping performed with 3F7.1 shows reactivity to amino acid sequences SEQ ID NO:14 and SEQ ID NO:15. The second LTP1 antibody, identified as 2C12.1 has very strong reactivity to LTP1, no reactivity to fLTP, and no reactivity to Protein Z. Epitope mapping performed with 2C12.1 shows reactivity to amino acid sequences SEQ ID NO:14 and SEQ ID NO:15, and a low level of reactivity to LTP1 amino acid sequences SEQ ID NO:10 and SEQ ID NO:11. The third LTP1 antibody, identified as 3G1.1, has strong reactivity to LTP1, no reactivity to fLTP, and no reactivity to Protein Z. Epitope mapping performed with 3G1.1 shows reactivity to amino acid sequences SEQ ID NO:4, SEQ ID NO:5, and SEQ ID NO:6.

The present invention also includes monoclonal antibodies against the denatured form of barley lipid transfer protein 1 isolated from beer foam (fLTP). The first fLTP antibody, identified as 3D1.1, has strong reactivity to fLTP, some reactivity to LTP1, and no reactivity to Protein Z. Epitope mapping performed with 3D1.1 shows strong reactivity to amino acid sequences SEQ ID NO:2, SEQ ID NO:3, and SEQ ID NO:4. The second fLTP antibody, identified as 2E3.1 has strong reactivity to fLTP, no reactivity to LTP1, and some unconfirmed reactivity to Protein Z. Epitope mapping performed with 2E3.1 shows reactivity to amino acid sequences SEQ ID NO:16 and SEQ ID NO:17. The third fLTP antibody, identified as 3D11.1, has weak reactivity to fLTP, no reactivity to LTP1, and no reactivity to Protein Z. Epitope mapping performed with 3D11.1 shows reactivity to amino acid sequences SEQ ID NO:4 and SEQ ID NO:5, and a low level of reactivity to SEQ ID NO:11, SEQ ID NO:12, SEQ ID NO:13, and SEQ ID NO:14.

In another embodiment, the present invention includes a kit comprising at least one LTP1 or fLTP antibody. In yet another embodiment, the present invention includes a kit comprising at least one LTP1 antibody and at least one fLTP antibody. In addition to the said antibodies, the kits may further comprise a 96-well plate, a sample-adsorbing buffer, a washing solution, a blocking solution, a substrate solution, a dilution of a secondary antibody and a calibration graph.

It is an object of the present invention to provide monoclonal antibodies useful in determining the content of both native lipid transfer proteins and denatured lipid transfer proteins in a foaming beverage during and after the beverage production process.

It is another object of the present invention to provide monoclonal antibodies that bind to native lipid transfer proteins and not denatured lipid transfer proteins.

It is another object of the present invention to provide monoclonal antibodies that bind to denatured lipid transfer proteins and not native lipid transfer proteins.

It is another object of the present invention to provide monoclonal antibodies that do not bind to protein Z.

It is one advantage of the present invention that foaming beverages can now be assayed to determine both the native lipid transfer protein content and the denatured lipid transfer protein content during various stages of the beverage production process.

Other objects, features and advantages of the present invention will become apparent after examination of the specification, claims and drawings.

DETAILED DESCRIPTION OF THE INVENTION

Figure 1:
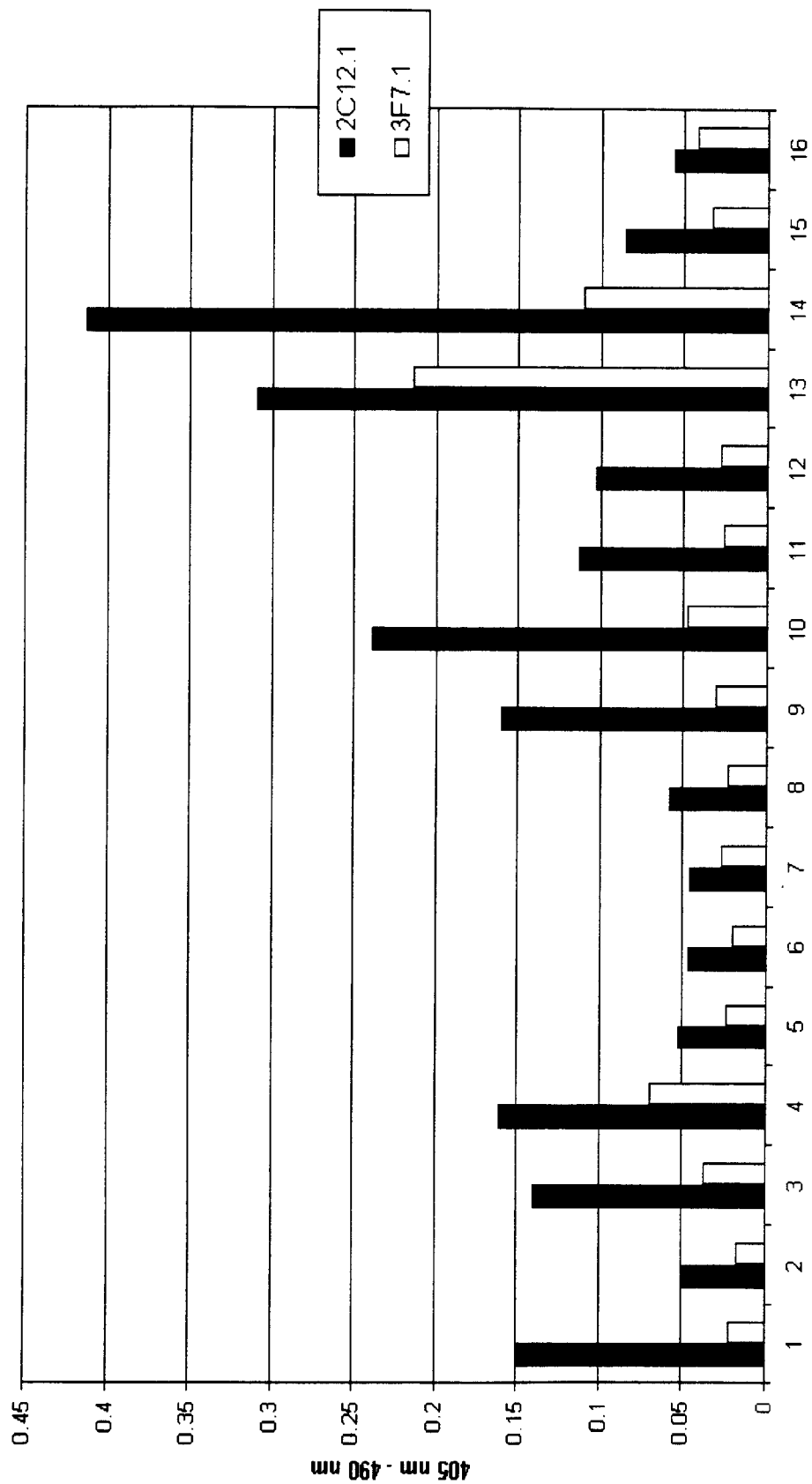
FIG. 1 is an epitope map for LTP1 antibodies 2C12.1 and 3F7.1

In accordance with the present invention, novel monoclonal antibodies against the native barley lipid transfer protein 1 (LTP1) and the denatured form of barley lipid transfer protein 1 (fLTP) are disclosed. Also disclosed is an immunoassay using said monoclonal antibodies.

The LTP1 and fLTP antibodies of the present invention can be used to isolate, measure and characterize the lipid transfer protein to which they bind. These proteins may include, without limitation, those proteins and polypeptides from plants which have a binding region specific to the antigen-binding region of the monoclonal antibodies of the present invention. For example, such proteins may include the lipid transfer proteins from cereal grains and, in particular, the lipid transfer protein from barley.

The monoclonal antibodies of the present invention can be produced using well-established hybridoma techniques first introduced by Kohler and Milstein (see, Kohler and Milstein, "Continuous Cultures of Fused Cells Secreting Antibody of Pre-Defined Specificity", *Nature*, 256:495–97 (1975)). These techniques involve the injection of an immunogen (e.g., cells or cellular extracts carrying the antigen or purified antigen) into an animal (e.g., mouse) so as to elicit a desired immune response in that animal. After a sufficient time, antibody-producing lymphocytes are obtained from the animal either from the spleen, lymph nodes or peripheral blood. Preferably, lymphocytes are obtained from the spleen. The splenic lymphocytes are then fused with a myeloma cell line, usually in the presence of a fusing agents such as polyethylene glycol (PEG). Any number of myeloma cell lines may be used as a fusion partner according to standard techniques. For example, one such myeloma cell line may include Sp2/0-Ag14 myeloma, non-secreting, mouse cell line (ATCC CRL 1581).

The resulting cells, which include the desired hybridomas, are then grown in a selective medium, such as HAT medium. In this medium, only successfully fused hybridoma cells survive while unfused parental myeloma or lymphocyte cells die. The surviving cells are then grown under limiting conditions to obtain isolated clones and their supernatents screened for the presence of antibodies having a desired specificity. Positive clones may then be subcloned under limiting dilution conditions and the desired monoclonal antibodies isolated. Hybridomas produced according to these methods can be propagated in vitro or in vivo (in ascites fluid) and purified using common techniques known in the art. Methods for purifying monoclonal antibodies include ammonium sulfate precipitation, ion exchange chromatography, and affinity chromatography (see, e.g., Zola et al., "Techniques for the Production and Characterization of Monoclonal Hybridoma Antibodies", in *Monoclonal Hybridoma Antibodies: Techniques and Applications*, pp. 51–52 (Hurell, ed., CRC Press, 1982)).

Once purified monoclonal antibodies are obtained, epitope mapping may be performed to determine which peptide segment (or antigen-binding region) of the protein is recognized by each particular antibody. The purpose for the epitope mapping is to have a well characterized monoclonal antibody. Ideally, monoclonal antibodies with different specificity to the same protein can be prepared so that researchers have probes for different parts of the protein under investigation.

The monoclonal antibodies of the present invention were produced via the hyridoma techniques described in the examples below using an Sp2/0-Ag14 myeloma, non-secreting, mouse cell line (ATCC CRL 1581). The hybridomas producing the monoclonal antibodies of the present invention were deposited with the American Type Culture Collection (ATCC), 10801 University Blvd., Manassa, Va. 20110–2209, on Sep. 15, 2000 and their monoclonal antibodies are identified as follows:

LTP1 antibody 3F7.1 (ATCC Accession No. PTA-2475)

The LTP1 antibody 3F7.1 displays a high specificity to LTP1 and no reactivity to fLTP or protein Z. Epitope mapping performed with LTP1 antibody 3F7.1 against linear peptide sequences from barley lipid transfer protein 1 exhibited reactivity with amino acid sequence LNLNNAASIPSKCNVNV (SEQ ID NO:14) and amino acid sequence AASIPSKCNVNVPYTIS (SEQ ID NO:15), encompassing one of LTP1's four alpha helices.

LTP1 antibody 2C12.1 (ATCC Accession No. PTA-2472),

The LTP1 antibody 2C 12.1 displays a high specificity to LTP1 and no reactivity to fLTP or protein Z. Epitope mapping performed with LTP1 antibody 2C12.1 against linear peptide sequences from barley lipid transfer protein 1 exhibited reactivity with amino acid sequence LNLNNAASIPSKCNVNV (SEQ ID NO:14) and amino acid sequence AASIPSKCNVNVPYTIS (SEQ ID NO:15), encompassing one of LTP1's four alpha helices. LTP1 antibody 2C12.1 also exhibited a lesser level of reactivity to amino acid sequence SGDRQTVCNCLKGIARG (SEQ ID NO:10) and amino acid sequence TVCNCLKGIARGIHNLN (SEQ ID NO:11), and possible reactivity with amino acid sequence LNCGQVDSKMKPCLTYV (SEQ ID NO:2), amino acid sequence KPCLTYVQGGPGPSGEC (SEQ ID NO:4), and amino acid sequence YVQGGPGPSGECCNGVR (SEQ ID NO:5).

LTP1 antibody 3G1.1 (ATCC Accession No. PTA-2476)

The LTP1 antibody 3G1.1 displays a high specificity to LTP1 and no reactivity to fLTP or protein Z. Epitope mapping performed with LTP1 antibody 3G1.1 against linear peptide sequences from barley lipid transfer protein 1 exhibited reactivity with amino acid sequence KPCLTYVQGGPGPSGEC (SEQ ID NO:4), amino acid sequence YVQGGPGPSGECCNGVR (SEQ ID NO:5), amino acid sequence PGPSGECCNGVRDLHNQ (SEQ ID NO:6), and amino acid sequence ECCNGVRDLHNQAQSSG (SEQ ID NO:7).

fLTP antibody 3D1.1 (ATCC Accession No. PTA-2473)

The fLTP antibody 3D1.1 displays a high specificity to fLTP, some LTP1 cross-reactivity, no cross-reactivity to protein Z, and no cross-reactivity with LTP1 when conjugated with alkaline phosphatase. Epitope mapping performed with fLTP antibody 3D1.1 against linear peptide sequences from barley lipid transfer protein 1 exhibited reactivity with amino acid sequence LNCGQVDSKMKPCLTYV (SEQ ID NO:2), amino acid sequence VDSKMKPCLTYVQGGPG (SEQ ID NO: 3), and amino acid sequence KPCLTYVQGGPGPSGEC (SEQ ID NO:4), which encompasses the N-terminus of the barley lipid transfer protein.

fLTP antibody 2E3.1 (ATCC Accession No. PTA-2474)

The fLTP antibody 2E3.1 displays a high specificity with fLTP and no LTP1 cross reactivity. Protein Z cross-reactivity was found by ELISA but was not confirmed by epitope mapping. Epitope mapping performed with fLTP antibody 2E3.1 against linear peptide sequences from barley lipid transfer protein 1 exhibited reactivity with amino acid sequence SKCNVNVPYTISPDIDC (SEQ ID NO:16) and amino acid sequence VNVPYTISPDIDCSRIY (SEQ ID NO:17), encompassing the LTP1's C-terminus.

fLTP antibody 3D11.1 (ATCC Accession No. PTA-2477).

The fLTP antibody 3D11.1 displays weak fLTP reactivity, but no cross reactivity to LTP1. Furthermore, fLTP antibody 3D11.1 shows no cross-reactivity to other types of foam proteins such as protein Z. Epitope mapping performed with fLTP antibody 3D11.1 against linear peptide sequences from barley lipid transfer protein 1 exhibited reactivity to amino acid sequence KPCLTYVQGGPGPSGEC (SEQ ID NO:4), amino acid sequence YVQGGPGPSGECCNGVR (SEQ ID NO:5). Additionally reactivity was observed towards amino acid sequence TVCNCLKGIARGIHNLN (SEQ ID NO:11), amino acid sequence LKGIARGIHNLNLNNAA (SEQ ID NO:12), amino acid sequence RGIHNLNLNNAASIPSK (SEQ ID NO:13), and amino acid sequence LNLNNAASIPSKCNVNV (SEQ ID NO:14). It is believed that this antibody may have reactivity toward an intermediate between native LTP1 and the denatured fLTP.

The term "LTP1 antibody" as used herein includes whole, intact monoclonal antibody materials such as the 3F7.1, 2C12.1, and 3G1.1 monoclonal antibodies described above. The LTP1 antibody also includes any fragments prepared therefrom containing the active antigen-binding region of such antibodies, using techniques well established in the art.

Likewise, the term "fLTP antibody" as used herein includes whole, intact monoclonal antibody materials such as the 3D1.1, 2E3.1, and 3D11.1 monoclonal antibodies described above. The fLTP antibody also includes any fragments prepared therefrom containing the active antigen-binding region of such antibodies, using techniques well established in the art.

In addition, the present invention encompasses antibodies that are capable of binding to the same antigenic determinant as either the LTP1 or fLTP antibodies and competing with the antibodies for binding at that site. These include antibodies having the same antigenic specificity as either the LTP1 or fLTP antibodies but differing in species origin, isotype, binding affinity or biological functions. For example, it is known that other plants, and in particular cereal grains, possess a lipid transfer protein homologous to the barley lipid transfer protein (see, Bech et al., EP 0728188B1, filed Aug. 11, 1994). These plants include, without limitation, almond, apple, apricot, Arabidopsis, bell pepper, carrot, castor bean, cauliflower, chickpea, cotton, Indian finger millet, kidney bean, Loblolly pine, maize, pea, peach, rape, rice, sorghum, spinach, sugar beet, sunflower, tobacco, and tomato.

The monoclonal antibodies of the present invention can be used to determine foam protein contents in final beer products and beer samples during the brewing process using an immunoassay. The immunoassay which may be employed includes, without limitations, radioimmunoassay, enzyme immunoassay, fluoroimmunoassaay, luminescent immunoassay, and turbidimetric immunoassay, among others. In particular the enzyme-linked immunosorbent assay (ELISA) is preferred because it provides highly sensitive detection and the automatic determination of a number of samples.

According to ELISA, a monoclonal antibody of the present invention is first immobilized as a primary antibody on a support. The support is preferably a solid support, for example, in the form of a container such as an ELISA plate molded from a polymer such as styrene or polystyrene. Immobilization of the monoclonal antibody on a support can be accomplished by, for example, adsorbing the monoclonal antibody dissolved in a buffer such as carbonate or borate buffer to the support. A polyclonal antibody may then be used as a secondary antibody to perform sandwich ELISA. Alternatively, foam proteins can be detected more reliably and exactly by applying sandwich ELISA using one of the monoclonal antibodies of the present invention as a primary antibody and a different monoclonal antibody as a secondary antibody, as described in the examples below.

The present invention also encompasses kits for carrying out the assays. The kit may comprise at least one LTP1 antibody and/or at least one fLTP antibody, or fragments thereof; a conjugate comprising a specific binding partner for the LTP1 antibody and/or fLTP antibody; and a label capable of producing a signal. Reagents may include ancillary agents such as buffering agents and protein stabilizing agents (e.g., polysaccharides). The kit may further comprise, when necessary, other components of the signal-producing system including agents for reducing background interference, control reagents, or an apparatus or container for conducting the test. In another embodiment, the kit comprises at least one LTP1 antibody and at least one fLTP antibody. Ancillary agents as mentioned above can also be present.

Because there may exist some homology between the lipid transfer proteins of various plant species, it is envisioned that the LTP1 or fLTP antibodies may also be useful in immunoassays directed at isolating, measuring, or characterizing the lipid transfer proteins from such plants. For example, cereal grains such as maize, rice, and wheat are also used to produce beer. Accordingly, the LTP1 and/or fLTP antibodies of the present invention may be useful in immunoassays directed at determining the LTP1 and/or fLTP content of such beers during various stages of their production. In addition, it is also envisioned that the LTP1 or fLTP antibodies may also find use in measuring the presence and levels of certain lipid transfer proteins (e.g., apple and peach) believed to be food allergens.

The nonlimiting examples that follow are intended to be purely illustrative.

EXAMPLES

Preparation of LTP1 and fLTP Monoclonal Antibodies

Monoclonal antibodies were successfully prepared against the native form of barley lipid transfer protein 1 (LTP1) and the denatured form of barley lipid transfer protein 1 isolated from beer foam (fLTP), using balb/c mice inoculated with solutions of purified LTP1 or fLTP. The purified solutions of LTP1 or fLTP were first prepared in 1 mg/ml aliquots using a 1×DPBS buffer. An aluminum hydroxide adjuvant (Superfos Biosector) was then added to 0.02% v/v and balb/c mice inoculated. Inoculation was performed by injecting new or previously immunized balb/c mice (at least 8 week old mice) with 200 ug of either the LTP1 solution or the fLTP solution on days 1, 7, 8, and 9. Inoculated mice were then sacrificed on day 10 and their splenocytes isolated.

The splenocytes isolated from the sacrificed mice were then fused with sp2/0 mouse myeloma cells using the method described by Oi and Herzenberg, "Selected methods in Cellular Immunology," pp. 357–359 (B. B. Mishell and S. Shigii (eds.) Freeman & Co., San Francisco, Calif. 1977). Successful fusion growth was selected for using azaserine (Sigma) in OPI-HT (Sigma) complete conditioned media with balb/c mouse feeder cells. Of the successfully fused myeloma cells, eighteen LTP1 antigen specific hybridoma clones and twenty fLTP antigen specific hybridoma clones were identified using enzyme-linked immunosorbent assays (ELISA). From these clones, monoclonal hybridomas were produced by infinity dilution subcloning and screened by ELISA.

Enzyme-Linked Immunosorbent Assays (ELISA)

The eighteen hybridoma clones to LTP1 and the twenty hybridoma clones to fLTP were analyzed using the ELISA method to determine their cross-reactivity to LTP1, fLTP and Protein Z. 96 well ELISA plates were coated overnight with fLTP, LTP1, protein Z, or recombinant human interferon gamma (negative control) antigen at 1 ug/well. The ELISA plates were blocked with 10% nonfat dry milk in 1×DPBS buffer for one hour and washed thoroughly. Specific antibody supemates were then added to the appropriate wells for 2 hours, followed by thorough washing. Alkaline Phosphatase conjugated Goat antimouse antibody (Sigma) specific to mouse IgG was added at 1:1000 dilution and allowed to incubate at room temperature for 1 hour. The plates were then thoroughly washed, and 50 ul of Sigma 104 color substrate (p-nitrophenyl phosphate, disodium, hexahydrate) was added for 2 hours (color development also occurs when the color substrate is 5-bromo-4 chloro-3-indolyl phosphate (BluePhos™, Kirkegaard & Perry Laboratories, Gaithersburg, Md.). 50 ul of IN NaOH was then added to stop color development and the ELISA plates were analyzed at 405 nm using an ELISA plate reader.

TABLE 1

ELISA reactivity and cross-reactivity date for LTP1 Antibodies

| LTP1 Clone | LTP1  | fLTP  | Protein Z | rH IFN Map |
|------------|-------|-------|-----------|------------|
| 1A3.1      | 1.116 | 0.261 | 0.242     | 0.169      |
| 1C3.1      | 1.413 | 0.397 | 0.363     | 0.239      |
| 1D4.1      | 1.068 | 0.144 | 0.237     | 0.219      |
| 1D6.1      | 0.188 | 0.231 | 0.211     | 0.247      |
| 1F3.1      | 1.698 | 0.195 | 0.208     | 0.14       |
| 2B2.1      | 1.401 | 0.204 | 0.242     | 0.134      |
| 2C12.1     | 1.432 | 0.192 | 0.173     | 0.201      |
| 2D2.1      | 1.16  | 0.288 | 0.262     | 0.198      |
| 2G6.1      | 1.173 | 0.305 | 0.257     | 0.226      |
| 2H1.1      | 1.186 | 0.279 | 0.417     | 0.217      |
| 3A9.1      | 1.624 | 0.241 | 0.177     | 0.118      |
| 3A11.1     | 1.476 | 0.142 | 0.14      | 0.111      |
| 3D10.1     | 1.452 | 0.202 | 0.14      | 0.149      |
| 3F7.1      | 1.544 | 0.162 | 0.187     | 0.203      |
| 3G1.1      | 1.018 | 0.245 | 0.274     | 0.165      |
| 3H4.1      | 1.331 | 0.19  | 0.252     | 0.162      |
| 3H7.1      | 1.567 | 0.244 | 0.302     | 0.189      |
| 4F5.1      | 1.851 | 0.213 | 0.218     | 0.186      |
| 4G1.1      | 0.174 | 0.166 | 0.207     | 0.103      |

TABLE 2

ELISA reactivity and cross-reactivity date for fLTP Antibodies

| fLTP Clone | LTP1  | fLTP  | Protein Z | rH IFN Map |
|------------|-------|-------|-----------|------------|
| 1A.1       | 0.279 | 0.429 | 0.215     | 0.189      |
| 1A3.1      | 0.191 | 0.547 | 0.292     | 0.871      |
| IG10.1     | 0.573 | 1.615 | 1.033     | 0.198      |
| 1H2.1      | 0.841 | 1.414 | 0.396     | 0.245      |
| 1H4.1      | 0.441 | 1.364 | 0.812     | 0.273      |
| 1H6.1      | 0.132 | 0.825 | 0.385     | 0.095      |
| 1H7.1      | 1.292 | 1.515 | 1.55      | 0.77       |
| 2A1.1      | 0.521 | 1.759 | 0.91      | 0.114      |
| 2C1.1      | 0.702 | 1.684 | 0.233     | 0.096      |
| 2E3.1      | 0.13  | 1.56  | 0.45      | 0.073      |
| 2G9.1      | 0.158 | 1.611 | 0.767     | 0.078      |
| 2H6.1      | 0.84  | 0.97  | 1.113     | 0.85       |
| 2H12.1     | 0.111 | 0.711 | 0.342     | 0.083      |
| 3B11.1     | 0.393 | 1.473 | 0.563     | 0.161      |
| 3D1.1      | 0.495 | 1.543 | 0.162     | 0.099      |
| 3D11.1     | 0.186 | 0.429 | 0.176     | 0.146      |
| 3F1.1      | 0.135 | 0.555 | 0.688     | 0.091      |
| 3G2.1      | 0.099 | 0.408 | 0.13      | 0.088      |
| 3H3.1      | 0.116 | 0.405 | 0.492     | 0.118      |
| 3H7.1      | 0.105 | 0.402 | 0.124     | 0.089      |

Epitope Mapping

Epitope mapping was performed with seven LTP1 antibodies and ten fLTP antibodies from LTP1 and fLTP hybridoma clones selected based upon their ELISA reactivity and cross reactivity data. Epitope mapping was performed using Chiron's Multipin™ synthesis technology and Pepset™ peptide libraries for both barley lipid transfer protein 1 (LTP1) and protein Z. The amino acid sequence for LTP1 is set forth in SEQ ID NO:1. The amino acid sequences for the epitope peptides used for the mapping procedure are set forth in SEQ ID NOS:2–17. Epitope mapping was carried out by the method recommended by Chiron Technologies. Geysen et al., "Strategies for epitope analysis using peptide synthesis," *J. Immunol. Methods*, 102:259–274 (1987).

The LTP1 monoclonal antibodies gave epitope maps with lower absorbance values than the fLTP mapos. It is believe that this is because the Chiron immobilized PepSets employ linear peptides and the LTP1 antibodies were searching for 3D structures.

Figure 2:
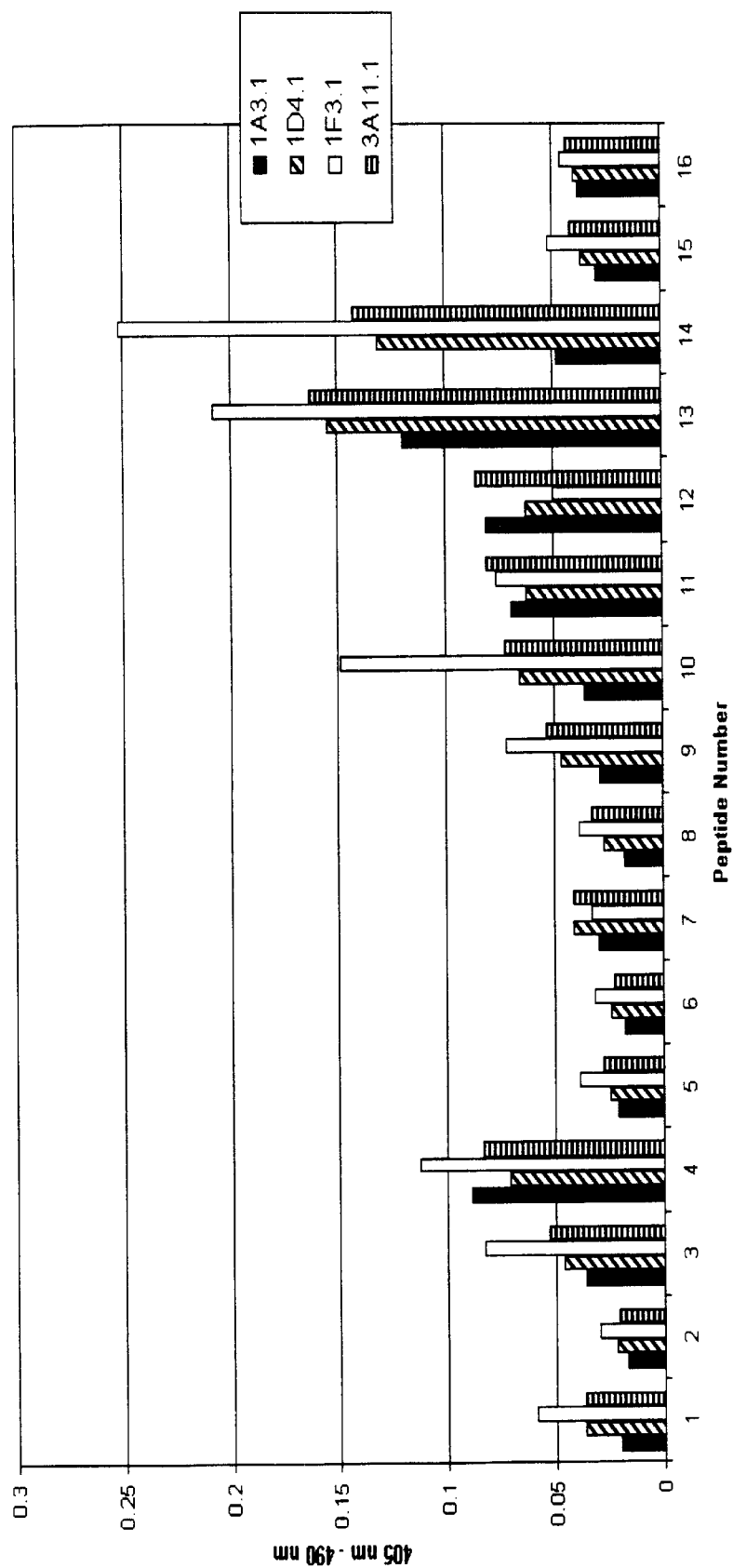
FIG. 2 is an epitope map for LTP1 antibodies 1A3.1, 1D4.1, 1F3.1 and 3A11.1.
Figure 3:
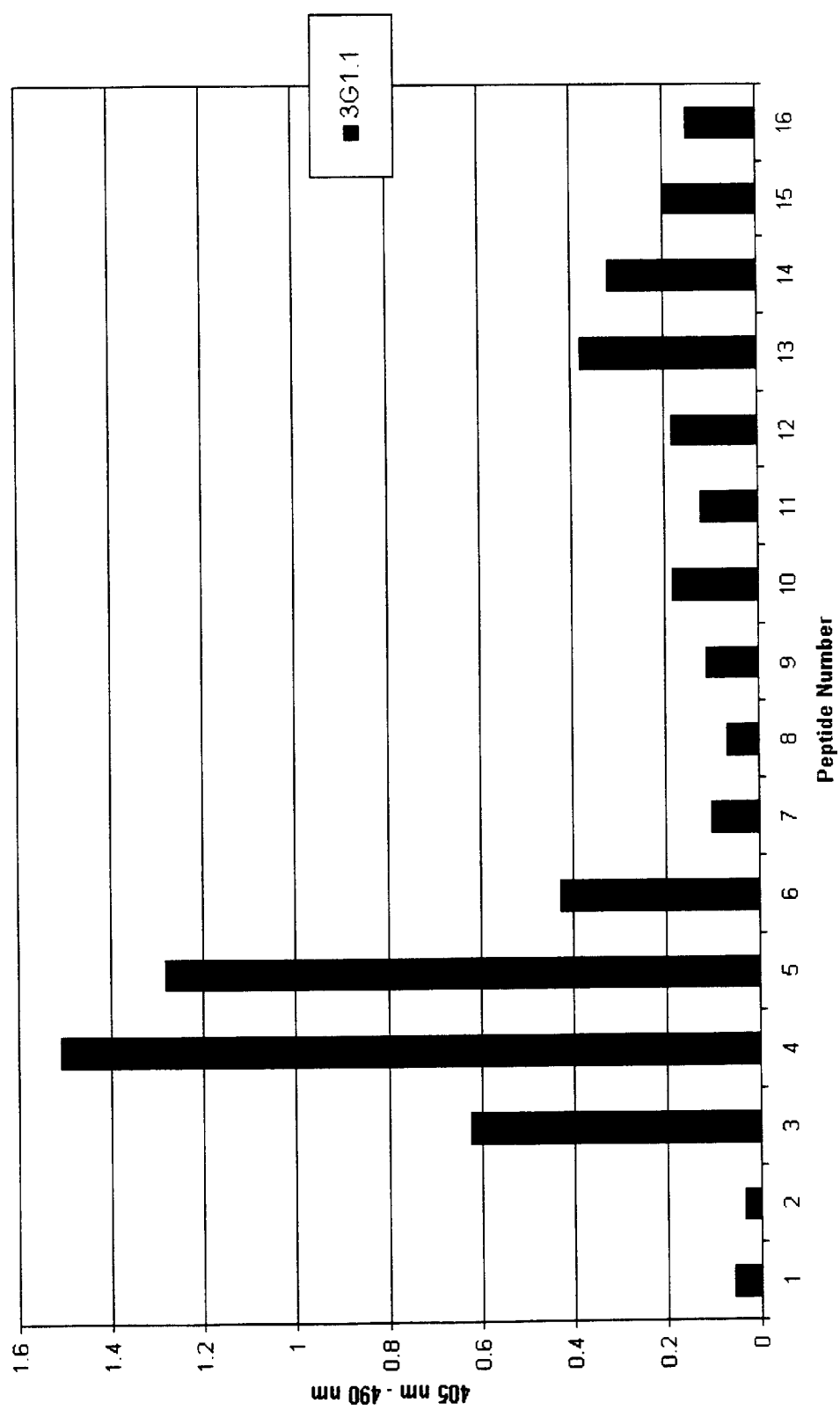
FIG. 3 is an epitope map for LTP1 antibody 3G1.1.

FIGS. 1, 2 and 3 illustrate the epitope profiles of the seven LTP1 antibodies selected for epitope mapping. Six of the seven LTP1 antibodies (2C12.1, 3F7.1, 1A3.1, 1D4.1, 1F3.1, and 3A11.1) gave similar profiles with the greatest response to peptide 13 (SEQ ID NO: 14) and peptide 14 (SEQ ID NO:15). FIGS. 1 and 2. These two peptides encompass one of the LTP1's four alpha helices. FIG. 1 depicts the epitope map for LTP1 antibodies 2C12.1 and 3F7.1. As illustrated, LTP1 antibody 2C12.1 exhibited reactivity with peptides 13 and 14, and lesser reactivity with peptides 9 and 10 (SEQ ID NOS: 10 and 11), and possible reactivity with peptides 1, 3 and 4 (SEQ ID NOS: 2, 4 and 5).

Figure 4:
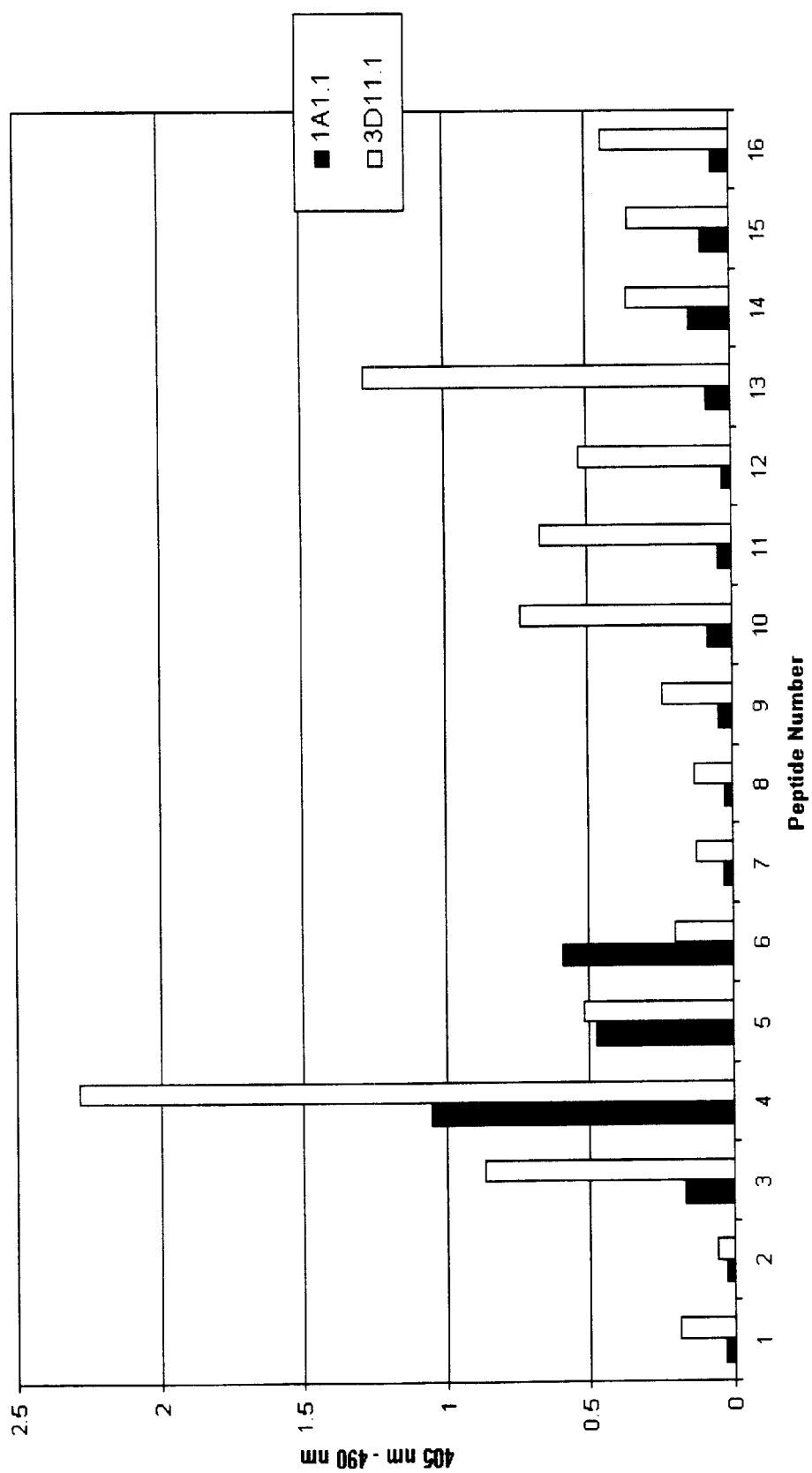
FIG. 4 is an epitope map for fLTP antibodies 1A1.1 and 3D11.1

The profile for the seventh LTP1 antibody (3G1.1) is depicted in FIG. 3, which shows strong reactivity with peptide sequences 3–6 (SEQ ID NOS:4–7). The map for this last LTP1 antibody was noted to be similar to the fLTP map of 1A1.1 and a portion of the fLTP map of 3D11.1. FIG. 4. Accordingly, it was deduced that LTP1 antibody 3G1.1 may not be toward a truly native structure, but an intermediate protein between the native and denatured states.

FIGS. 4, 5, 6, and 7, illustrate the epitope profiles of the ten fLTP antibodies selected for epitope mapping. FIG. 4 depicts the epitope map for fLTP antibodies 1A1.1 and 3D11.1. As indicated above, this map was very similar to the epitope map for LTP1 antibody 3G1.1. Unlike LTP1 antibody 3G1.1, fLTP antibodies are most certainly not toward native LTP1, but are directed against LTP1 in its denatured state. The fLTP map for 3D11.1 has the same points of similarity as 1A1.1, but also reacts strongly with peptides 10–13 (SEQ ID NOS:11–14). Accordingly, it was deduced that fLTP antibody 3D11.1 probably contained at least two clones or, in the alternative, has reactivity towards an intermediate LTP1 conformation.

Figure 5:
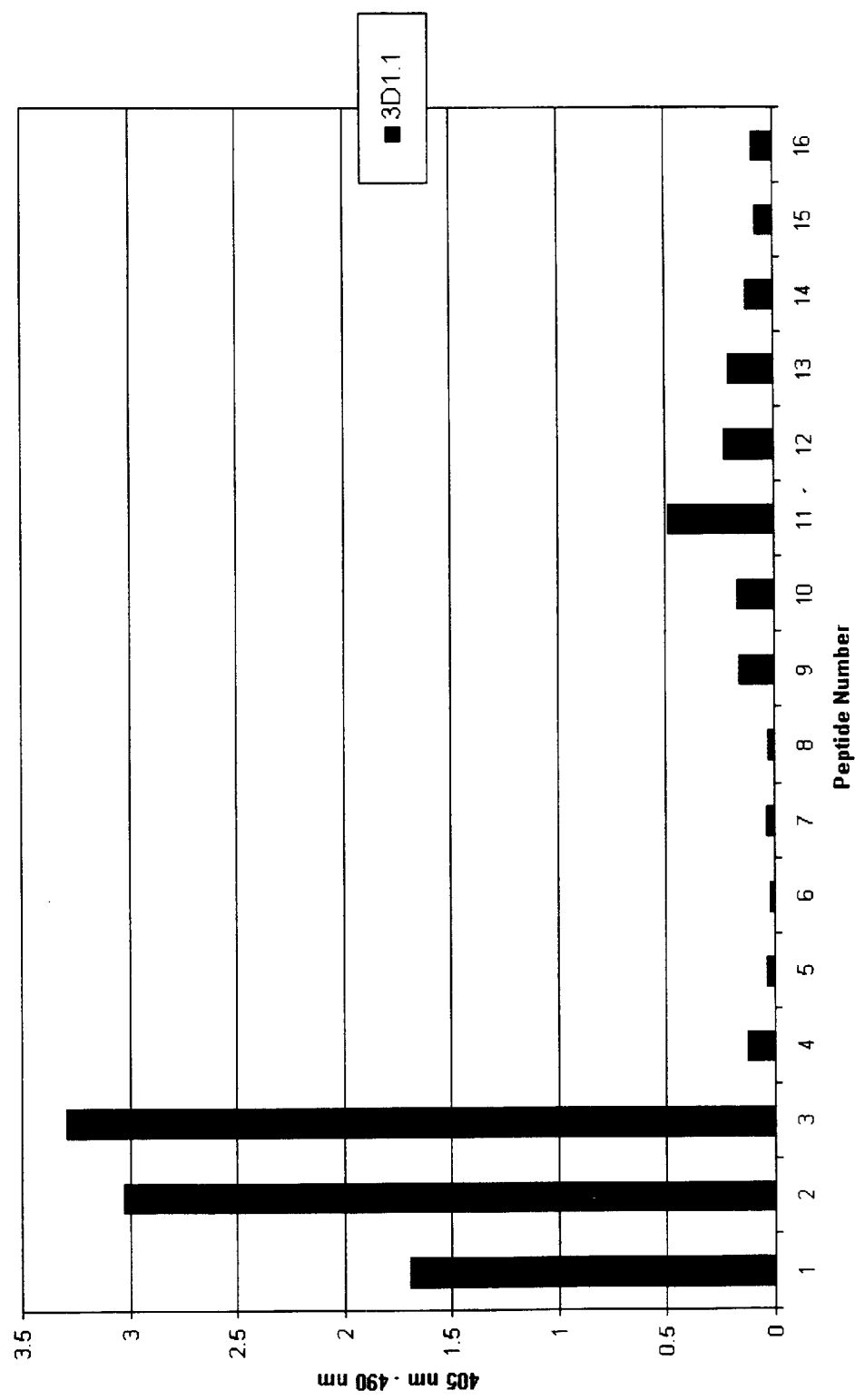
FIG. 5 is an epitope map for fLTP antibody 3D1.1

FIG. 5 depicts the epitope map for fLTP antibody 3D1.1. As illustrated in FIG. 5, fLTP antibody 3D1.1 reacted very strongly with peptides 1–3 (SEQ ID NO:2–4). Peptides 1–3 encompass the N-terminus of LTP1 in its denatured form.

Figure 6:
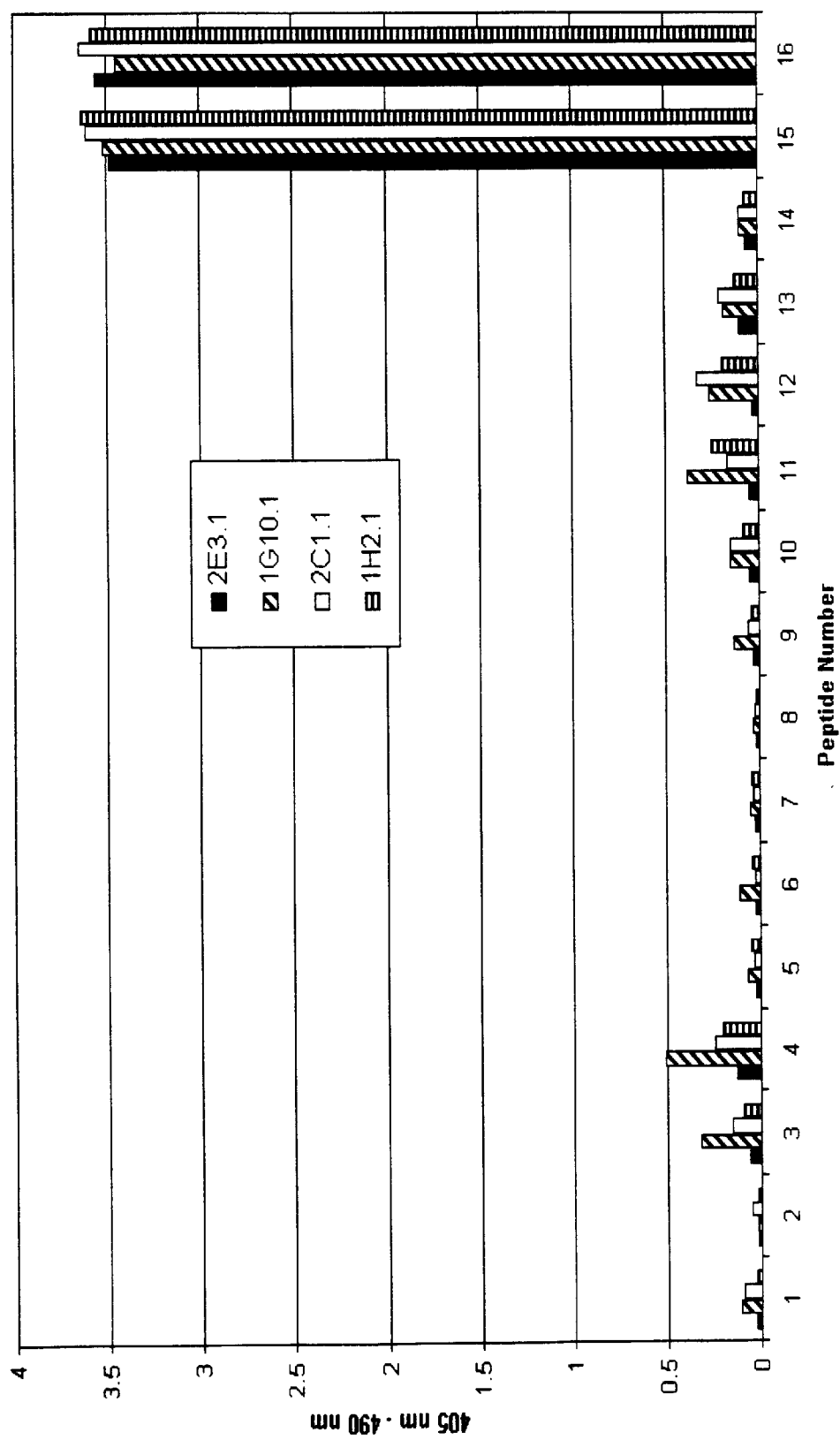
FIG. 6 is an epitope map for fLTP antibodies 2E3.1, 1G10.1, 2C1.1 and 1H2.1

FIG. 6 depicts the epitope map for fLTP antibodies 2E3.1, 1G10.1, 2C1.1, and 1H2.1. These four fLTP antibodies reacted strongly with the C-terminus peptides 15 and 16 (SEQ ID NO: 5 and 6).

Figure 7:
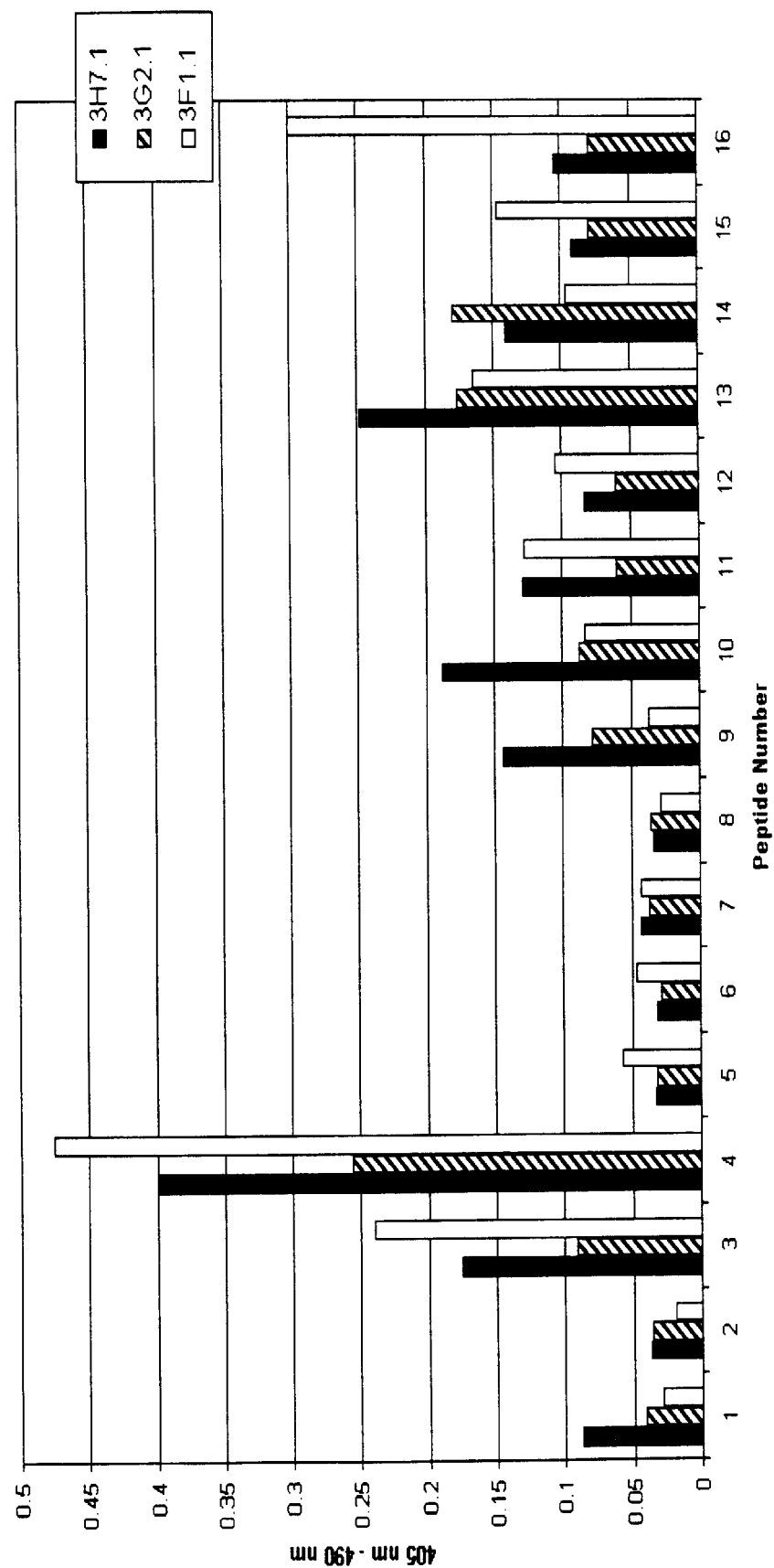
FIG. 7 is an epitope map for fLTP antibodies 3H7.1, 3G2.1 and 3F1.1

FIG. 7 depicts the epitope map for fLTP antibodies 3H7.1, 3G2,1 and 3F1.1. These three fLTP antibodies reacted poorly with all of the peptide sequences.

Figure 8:
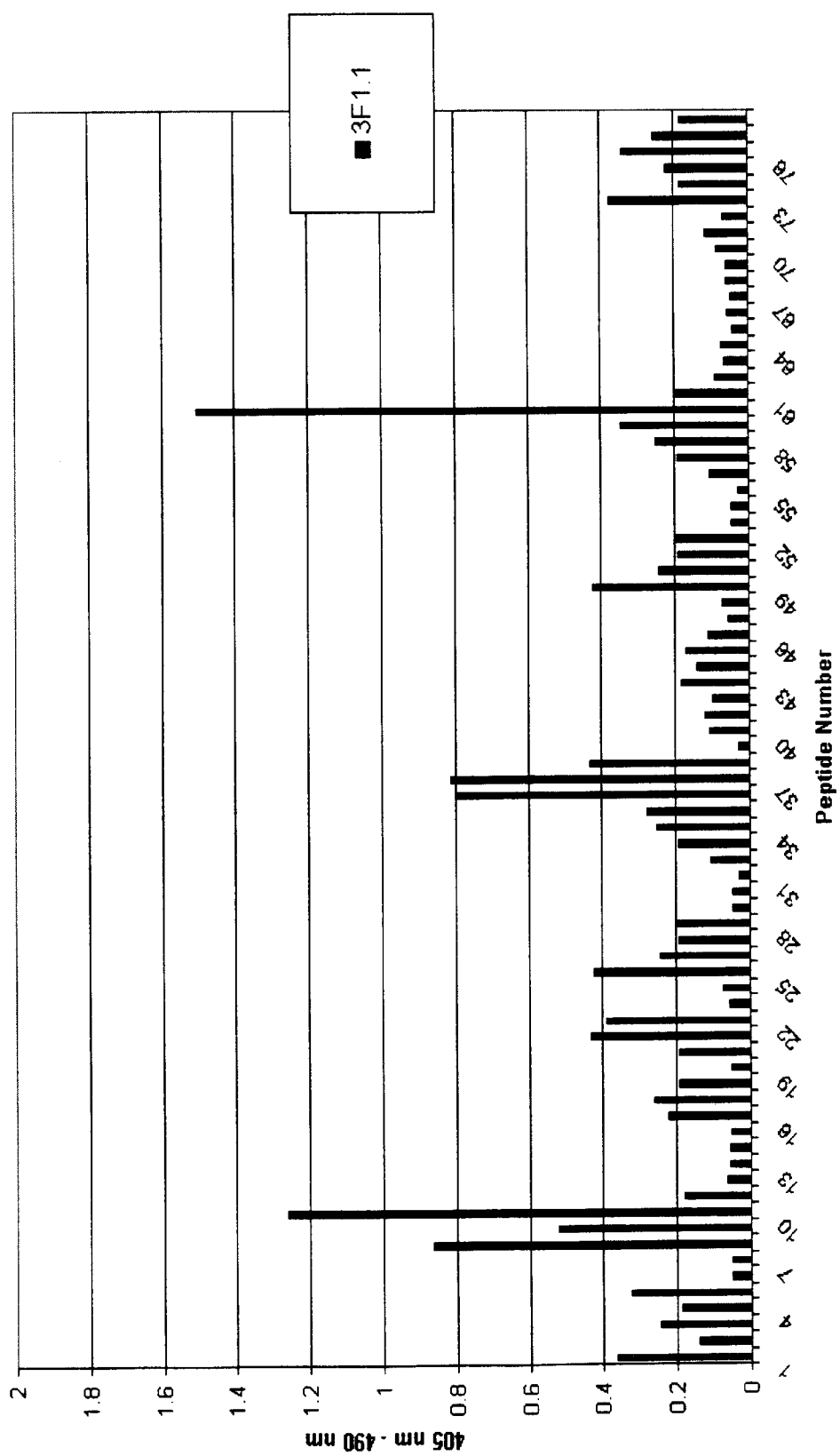
FIG. 8 is a protein Z epitope map for fLTP antibodies 3F1.1.
Figure 9:
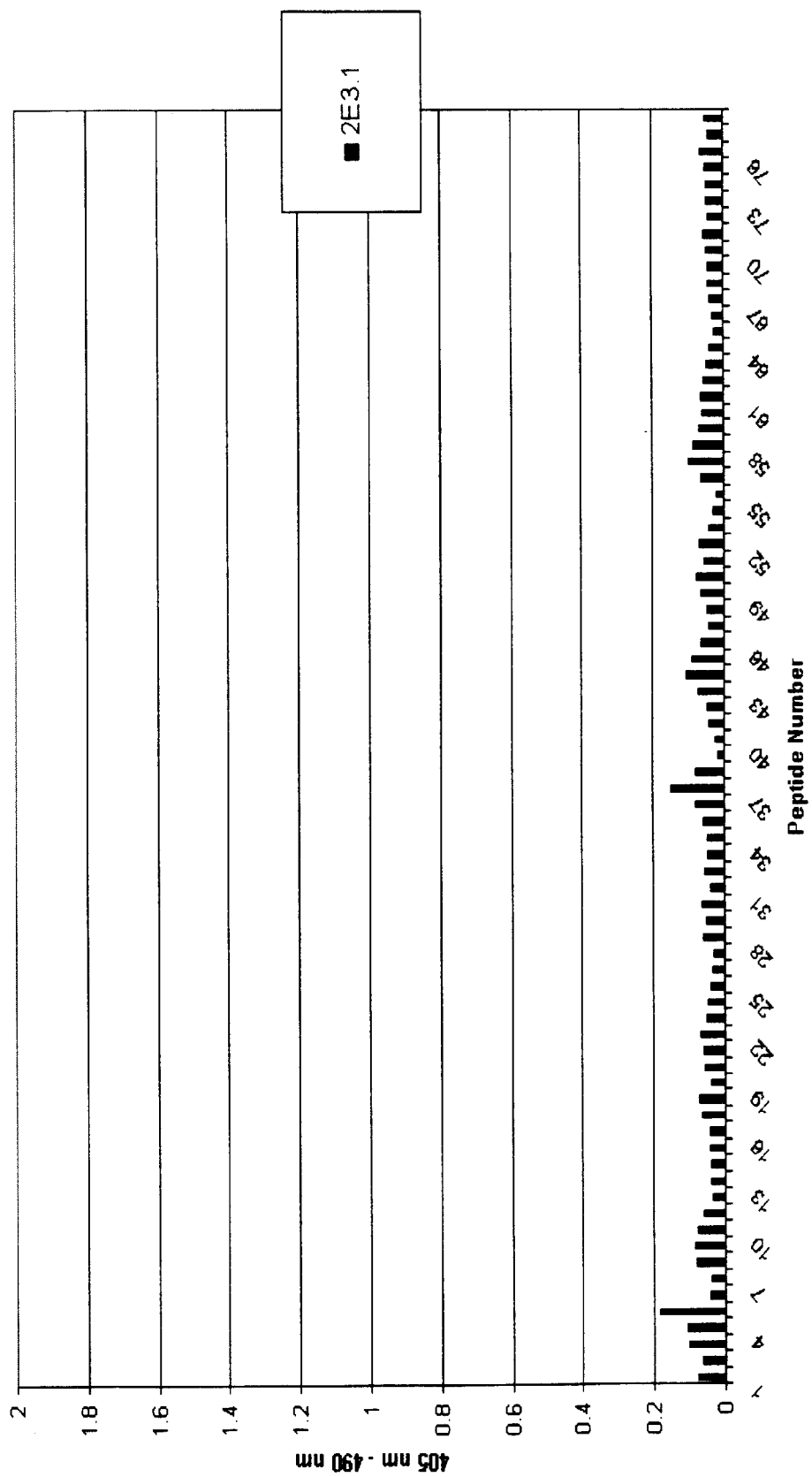
FIG. 9 is a protein Z epitope map for fLTP antibodies 2E3.1.
Figure 10:
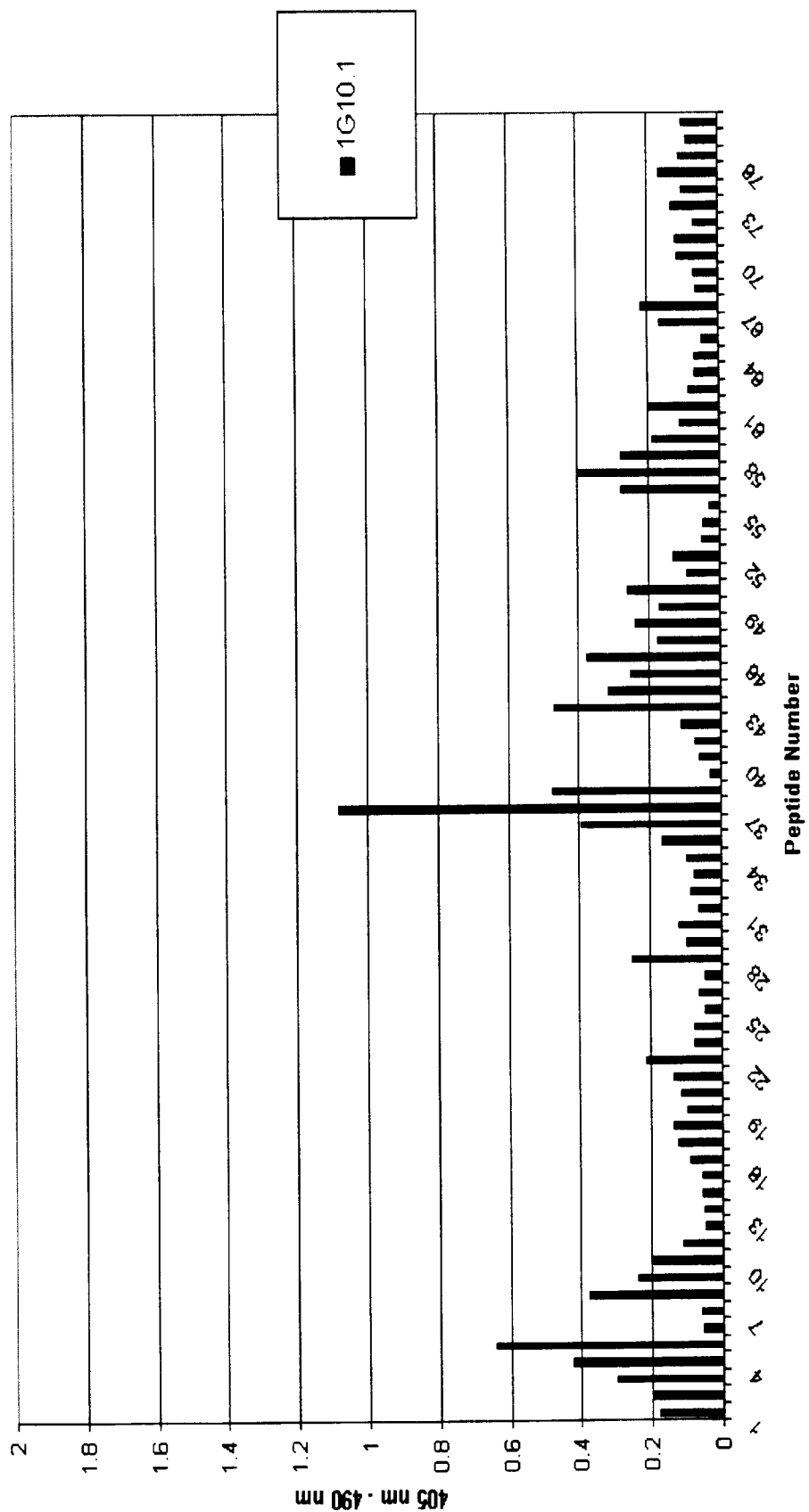
FIG. 10 is a protein Z epitope map for fLTP antibodies 1G10.1.

Maps were also made of the cross reactivity of fLTP antibodies prepared to protein Z. FIGS. 8, 9, 10 depict the epitope map for these fLTP antibodies. As illustrated, fLTP clone 2E3.1 showed no cross reactivity, while fLTP antibodies 3F1.1 and 1G10.1 showed some cross-reactivity for protein peptides 37–39.

Taken together, these results indicate that monoclonal antibodies specific to either LTP1 or fLTP have been purified and isolated. Accordingly, monoclonal antibodies capable of use in immunoassays to determine the content of native and denatured barley lipid transfer protein have been obtained.

We claim:

1. A monoclonal antibody produced by a hybridoma selected from the group consisting of hybridoma 3F7.1 having ATCC accession number PTA-2475, hybridoma 2C12.1 having ATCC accession number PTA-2472, hybridoma 3G1.1 having ATCC accession number PTA-2476, hybridoma 3D1.1 having ATCC accession number PTA-2473, hybridoma 3D11.1 having ATCC accession number PTA-2477, and hybridoma 2E3.1 having ATCC accession number PTA-2474.

2. A fragment of the monoclonal antibody of claim 1, the fragment comprising at least a portion of the antigen-binding region of the monoclonal antibody, wherein said portion is able to bind to the same antigenic determinant as does the monoclonal antibody.

3. An assay kit comprising a first antibody produced by a hybridoma selected from the group consisting of hybridoma 3F7.1 having ATCC accession number PTA-2475, hybridoma 2C12.1 having ATCC accession number PTA-2472, hybridoma 3G1.1 having ATCC accession number PTA-2476, hybridoma 3D1.1 having ATCC accession number PTA-2473, hybridoma 3D11.1 having ATCC accession number PTA-2477, and hybridoma 2E3.1 having ATCC accession number PTA-2474, a first conjugate comprising a specific binding partner for the first antibody, and a label capable of producing a signal that identifies the presence of the first antibody.

4. The assay kit of claim 3 further comprising a second antibody produced by a hybridoma selected from the group consisting of hybridoma 3F7.1 having ATCC accession number PTA-2475, hybridoma 2C12.1 having ATCC accession number PTA-2472, hybridoma 3G1.1 having ATCC accession number PTA-2476, hybridoma 3D1.1 having ATCC accession number PTA-2473, hybridoma 3D11.1 having ATCC accession number PTA-2477, and hybridoma 2E3.1 having ATCC accession number PTA-2474, wherein the second antibody is different than the first antibody, a second conjugate comprising a specific binding partner for the second antibody.

5. An antigen-binding fragment that specifically binds to plant lipid transfer proteins, said antigen-binding fragment capable of binding to the same antigenic determinant as does a monoclonal antibody produced by a hybridoma selected from the group consisting of hybridoma 3F7.1 having ATCC accession number PTA-2475, hybridoma 2C12.1 having ATCC accession number PTA-2472, hybridoma 3G1.1 having ATCC accession number PTA-2476, hybridoma 3D1.1 having ATCC accession number PTA-2473, hybridoma 3D11.1 having ATCC accession number PTA-2477, and hybridoma 2E3.1 having ATCC accession number PTA-2474.

6. The antigen-binding fragment of claim 5 wherein the fragment is either a monoclonal antibody or a polyclonal antibody.

7. A hybridoma selected from the group consisting of hybridoma 3F7.1 having ATCC accession number PTA-2475, hybridoma 2C12.1 having ATCC accession number PTA-2472, hybridoma 3G1.1 having ATCC accession number PTA-2476, hybridoma 3D1.1 having ATCC accession number PTA-2473, hybridoma 3D11.1 having ATCC accession number PTA-2477, and hybridoma 2E3.1 having ATCC accession number PTA-2474.

* * * * *